United States Patent [19]

Chisolm et al.

[11] Patent Number: 5,015,777

[45] Date of Patent: May 14, 1991

[54] PROCESS FOR THE PREPARATION OF AROMATIC BETA-DIKETONES

[75] Inventors: Daniel R. Chisolm, Warwick, N.Y.; Richard A. Weiss, Parsippany; Leonid Rozov, Fairlawn, both of N.J.

[73] Assignee: Witco Corporation, New York, N.Y.

[21] Appl. No.: 430,563

[22] Filed: Nov. 2, 1989

[51] Int. Cl.$^5$ ............................................. C07C 45/45
[52] U.S. Cl. ..................................... 568/314; 568/42; 568/306; 549/446
[58] Field of Search .................... 568/314, 42, 306; 549/446

[56] References Cited

U.S. PATENT DOCUMENTS

| | | | |
|---|---|---|---|
| 3,362,935 | 1/1968 | Norton | 568/314 |
| 3,742,062 | 6/1973 | Chappelon et al. | 568/314 |
| 4,065,502 | 12/1977 | MacKay | 568/314 |
| 4,256,657 | 3/1981 | Wheeler | 568/314 |
| 4,482,745 | 11/1984 | Mauding | 568/314 |
| 4,562,067 | 12/1985 | Hopp et al. | 568/314 |

OTHER PUBLICATIONS

Swamer et al., J.A.C.S., vol. 72, pp. 1352–1356 (1950).

*Primary Examiner*—James H. Reamer
*Attorney, Agent, or Firm*—Lockwood, Alex, Fitzgibbon & Cummings

[57] ABSTRACT

A process for the preparation of aromatic beta-diketones by the reaction of an acetophenone and a molar excess of an alphatic ester or an ester of benzoic acid in the presence of sodium alkoxide condensation agent in an aromatic hydrocarbon solvent. Also disclosed is a method of recycling the solvent and excess ester reactant after separation of the aromatic beta-diketone product.

20 Claims, No Drawings

PROCESS FOR THE PREPARATION OF AROMATIC BETA-DIKETONES

BACKGROUND OF THE INVENTION

This invention generally relates to a process for the preparation of beta-diketones and, more particularly, to a process for the production of aromatic beta-diketones that permits recovery of high yields of product and efficient recirculation of solvent. An important aspect of this invention is directed to the preparation of dibenzoylmethane by the reaction of acetophenone and methyl benzoate in xylene solvent.

FIELD OF THE INVENTION

Beta-diketones are highly valuable compounds having advantageous utility in a wide variety of applications. For example, Aoki et al. U.S. Pat. No. 4,427,816 discloses beta-diketones in combination with hydrotalcites as stabilizer compositions for halogen containing polymers. Ebel U.S. Pat. No. 3,001,970 discloses the use of dibenzoylmethane to prevent the discoloration of vinylidene chloride. Weisfeld U.S. Pat. No. 3,493,536 discloses that diaroylmethane compounds provide stabilizing action against the sensitizing effect of bismuth or antimony compounds on chlorine containing materials. Aryl substituted beta-diketones are shown by Gontarz et al. U.S. Pat. No. 3,994,869 to be useful as accelerators for the photodegradation of polyolefins.

The preparation of beta-ketones a reported in *Organic Reactions* (Vol. 8, 1959), Chapter 3, (pages 59-195) entitled "The Acylation of Ketones to form B-diketones Or B-keto Aldehydes", states in its introduction at page 61, "Under certain conditions, a ketone having an α-hydrogen atom may be acylated with an ester, an acid anhydride, or an acid chloride to form a B-ketone or, when the acylating agent is a formic ester, B-keto aldehyde. The process consists in the replacement of an α-hydrogen atom of the ketone by an acyl group . . ."

Unfortunately, the acylation of ketones, as achieved by using previously known procedures, is a reaction that does not readily proceed in an economical manner. On page 66 of this same text, for example, it is pointed out that the acylation of ketones with esters in the presence of a basic reagent may be accompanied by certain side reactions. Included among these side reactions are self-condensation of the ketone; self-condensation of the ester; aldol reaction of the ester with the carbonyl group of the ketone or a Michael condensation of the ketone. Also, the basic condensing agent may react with the carbonyl group of the ester.

The preparation on a laboratory scale of dibenzoyl methane by the reaction of acetophenone and ethyl benzoate in the presence of sodium ethoxide and the absence of solvent is reported by Magnani and McElvain in Organic Synthesis, Collective Volume 3, pp. 251-253. This reaction used 4 moles of ethyl benzoate and 0.5 mole of acetophenone. The reaction mixture wa gelatinous after all of the ethoxide had been added and was too viscous to be stirred with a Hershberg stirrer. The yield of dibenzoyl methane recovered from the reaction mixture, as reported, was 62-71% based on the acetophenone.

In general, the reaction of the ester, the ketone and the basic condensing agent in the presence of an inert solvent is known as in the aforementioned *Organic Reactions* article at page 112. This article further states that the beta-diketone may be isolated by the usual technique of distillation or filtration but often it is isolated as its copper derivative from which the beta-diketones may be readily regenerated.

The use of copper derivatives is an expensive and environmentally undesirable procedure. Furthermore, the occurrence of side reactions would prevent the commercial success of the process. Then too loss of solvent and the need to use fresh solvent for each reaction is commercially unattractive.

Previously mentioned U.S. Pat. No. 3,994,869 discloses the preparation of aryl substituted beta-diketones by the reaction of acetophenone or a substituted acetophenone with an ester in the presence of a base such as sodium methoxide, sodium ethoxide and sodium hydride. The acetophenone may be represented by the following structural formula:

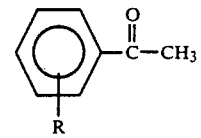

wherein R is selected from the group consisting of hydrogen, halogen, $C_1$ to $C_9$ alkyl and $C_1$ to $C_9$ alkoxy. Representative esters identified as useful in this reaction are methyl stearate, ethyl benzoate, ethyl acetate and ethyl laurate. This reaction, according to the patent, can be carried out in a suitable aprotic solvent such as toluene or tetrahydrofuran. Recovery of the desired product is stated to be by methods which are now known in the art.

While it has been known that beta-diketones can be made by the reaction of acetophenone or a substituted acetophenone with an ester in the presence of base this procedure has drawbacks which have limited its commercial acceptability. Maulding U.S. Pat. No. 4,482,745 discloses that handling large quantities of strong bases such as sodium ethoxide makes their use undesirable and costly for large scale production. Yet sodium alkoxides are preferred bases since half of the sodium alkoxide used is regenerated in the second step of the condensation whereas 2 moles of metallic sodium, sodium amide or sodium hydride would normally be required. Then too metallic sodium or sodium hydride are more hazardous than the alkoxides.

It is therefore an object of the present invention to prepare beta-diketones in high yields and purity.

Another object of the present invention is to provide a process for preparing beta-diketones that minimizes solvent requirements.

Still another object of the present invention is to provide a process that does no incur side reactions that would consume large amounts of reactant and intensify the recovery and purification procedures.

Another object of the present invention is to minimize the procedures required for the recovery and recirculation of solvent and excess reactant and at the same time permit the use of standard equipment so as to minimize capital requirements.

A yet further object of the present invention is to provide a process for the preparation of beta-diketones that does not require temperatures higher than those available by the use of steam heat.

Other objects of the present invention will become apparent from the following description.

SUMMARY OF THE INVENTION

The present invention provides an efficient process for the preparation of beta-diketones. This process involves the reaction of an acetophenone and either an ester of benzoic acid or an ester of an aliphatic acid having from about 12 to about 20 carbon atoms in the presence of a sodium alkoxide condensation agent in an aromatic hydrocarbon solvent at a temperature between about 120° C. and about 170° C.

DETAILED DESCRIPTION

The present process is for the preparation of aromatic beta-diketones having the structural formula:

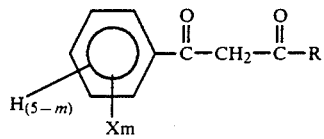

wherein X is selected from the group consisting of lower alkyl, lower alkoxy, lower alkylthio, chloro, bromo, nitro and methylenedioxy; m is an integer from 0-3 provided that only one X is nitro or methylenedioxy. R is $(CH_2)_p CH_3$ or

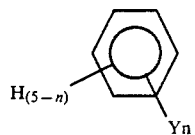

wherein p is an integer from about 11 to about 19; Y is selected from the group consisting of lower alkyl, lower alkoxy, lower alkylthio, chloro, bromo and nitro; n is an integer from 0-3, provided that only one Y is nitro.

This process comprises mixing an acetophenone having a structural formula which may be represented as follows:

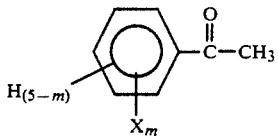

wherein X and m are as previously defined and a molar excess of a benzoic acid ester represented by the structural formula:

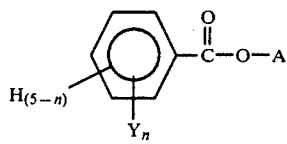

(1)

wherein Y and n are as previously described and A is lower alkyl or an alphatic acid ester represented by the structural formula:

(2)

wherein A and p are as previously described in the presence of a sodium alkoxide condensation agent in an aromatic hydrocarbon solvent at a temperature between about 120° C. and 170° C.

Aromatic beta-diketones in high yields and purity can be readily made by this process. Exemplary of such aromatic beta-diketones are dibenzoylmethane, benzoyl 2,4-methylenedioxy benzoylmethane; benzoyl 3,5-dimethylbenzoyl methane; benzoyl 3-methylbenzoylmethane; benzoyl 4-methyl benzoylmethane; 3-methylbenzoyl 4-methylbenzoylmethane; benzoyl 4-chlorobenzoylmethane; benzoyl 2-bromobenzoylmethane; benzoyl 3,5-dichlorobenzoylmethane; benzoyl 2-nitrobenzoylmethane; benzoyl-2,3,4-trimethylbenzoylmethane; benzoyl-2,3,5-trichlorobenzoylmethane; benzoylstearoylmethane; 3-methylbenzoylstearoylmethane 3,4-dichlorobenzoylstearoylmethane benzoyl heptadecanoylmethane; 3-methylbenzoyltetradecanoylmethane; 4-chloro-nonadecoylmethane; 2-methylbenzoylauroylmethane; 3-nitrobenzoylmyristoylmethane; 2,3-ethoxybenzoyl palmitoylmethane; 2-methoxy benzoylstearoylmethane, 3-methylthio benzoyl 2,3-butylmethane and the like.

An order to prepare these and other beta-diketones within the scope of the above shown structural formula, it is necessary to select the corresponding acetophenone for use in the process of this invention. Exemplary of useful acetophenone reactants are acetophenone; o-,m- or p-methylacetophenone; o,m- or p-methoxy acetophenone; o-,m-or p-methylthioacetophenone, o-, m- or p-nitroacetophenone; 3,4-(methylenedioxy) acetophenone, o-,m- or p-chloroacetophenone; o-,m- or p-bromoacetophenone; 2,4-diethylacetophenone; 2,3,5-trichloroacetophenone, 2,3-dibromoacetophenone; 2,4-dimethoxyacetophenone; 2,4-propxyacetophenone; 2,3-dimethylthioacetophenone and the like.

Similarly, the ester reactant need be selected on the basis of the identity of the desired beta-ketone. In the instances where a beta-diketone compound is desired, an ester of benzoic acid is to be used. Since this condensation reaction has as its by product an alcohol formed from the ester group, normally there is no benefit from using higher alkyl esters. Accordingly, lower alkyl ester of benzoic acid are satisfactory, although higher ester can be used. In this description of the invention the term "lower" means alkyl groups having up to about 5 carbon atoms.

Exemplary of this reactant are methylbenzoate; ethyl benzoate; propylbenzoate; butylbenzoate; pentylbenzoate; methyl o-,m- or p-methylbenzoate; ethyl o-,m- or p-chlorobenzoate; methyl o-,m- or p-methylthiobenzoate; ethyl o-,m- or p- methoxybenzoate; methyl o-,m- or p- bromobenzoate; ethyl o-,m- or p- nitrobenzoic acid; ethyl 2,3-dimethyl benzoate; propyl 2,5-diethylbenzoate; ethyl 2,3,4-tri-methylbenzoate; butyl-2,5-diethylthiobenzoate; ethyl 3,4-dimethoxybenzoate; methyl 2,3-dichlorobenzoate; ethyl 2,4-dibromobenzoate; propyl 2,3,5-trichlorobenzoate; propyl 2,4-diethyoxybenzoate and the like.

Beta-diketones having the above shown structural formula wherein R is $CH_3(CH_2)p$ - can be obtained by using as the ester reactant a lower alkyl ester of an alphatic acid having from about 12 to about 20 carbon atoms. As in the reaction using an alkyl ester of benzoic acid as a reactant, the reaction can be performed with esters having varying chain lengths but it is desirable to use lower alkyl esters since the alcohol by-product of the reaction will be a lower alcohol.

This reaction can be performed at various elevated temperatures. It has been found that in order to optimize the yield and purity of the aromatic beta-diketones product, temperatures between about 120° C. and about 170° C., preferably about 140° C. should be used. At these temperatures maximum amounts of high quality aromatic beta-diketone products can be recovered by standard procedures.

In order to obtain these high quality product in high yield it is desired to use a molar excess of the ester reactant. This causes the reaction to proceed to about its theoretical maximum. The preferred excess of ester reactant useful in this process varies somewhat with the identity of the ester reactant. Since the use of more than the necessary amount of ester reactant will often increase the loss of this reactant, it is preferred to maintain the ratio of ester reactant to acetophenone below about 8:1, more preferably below about 6:1. Ratios of the ester of benzoic acid to acetophenone of about 4:1 have shown to product optimum yields and purity of dibenzoylmethane. As an embodiment of this invention the excess ester reactant can be recycled with the solvent so as to limit the reactant needs and reduce the cost of operating the process.

Aromatic hydrocarbons can be used as solvent for performing this process. Since the temperature of the reaction is between about 120° C. and about 170° C., it is desirable to use an aromatic hydrocarbon solvent having a boiling point within this temperature range so that the reaction can proceed at atmospheric temperature; however, aromatic hydrocarbons having lower or higher boiling points can be used by adjusting the pressure accordingly. Among the aromatic hydrocarbons useful as solvent in the present process are ethyl benzene, cymene, diethylbenzene, dimethylethylbenzene, amyltoluene, toluene, trimethylbenzene and xylene.

Xylene is a particularly useful solvent since the reflux temperature of the present reaction mixture using xylene as the solvent at atmospheric pressure is about 140° C., the preferred reaction temperature. As the ensuing examples demonstrate not only does the reaction proceed at optimum efficiency in xylene solvent but it is also convenient to recover the xylene solvent and excess ester reactant without excessive equipment or elaborate processing. Thus the use of xylene permits good control of the reaction and recovery of the product by means known to the art for the separation of a solid product. Furthermore it permits reuse of the solvent and excess ester reactant.

Thus for maximum efficiency in the present process the solvent and excess ester reactant are separated from the beta-diketone product by means such as distillation and recycled into a second mixture of the acetophenone and the ester reactant. This recycling of the solvent and ester reactant can be repeated into a third mixture of the acetophenone and ester reactants and if desired into a fourth reaction mixture and continued as desired.

The reaction of the present invention is a condensation reaction. Thus, it need be performed in the presence of a condensation agent. While other condensation agent may be operable, sodium alkoxides are efficient condensation agents for this reaction. These alkoxides can be of various chain length. For most purposes alkoxides having up to about 4 carbon atoms will suffice, although longer groups can be used successfully. The amount of condensation agent can vary, although amounts from about equimolar to about a 25 percent molar excess or higher based on the moles of the acetophenone reactant can be used.

The following examples illustrate the performance of the present process, which is not limited thereto.

EXAMPLE 1

Preparation Of Dibenzoylmethane

Methylbenzoate (136.0 grams; 1.0 mol), acetophenone (30.0 grams; 0.25 mol), sodium methoxide (17.3 grams; 0.3 mol) and xylene (300 ml) were placed into a four-necked, round bottom, one liter flask equipped with stirrer, nitrogen addition adapter, thermometer and Oldershaw column connected with distillation head and a trap. The mixture was heated with stirring to 135°–140° C. and maintained there for 6 hours while under a blanket of nitrogen. At 110°–120° C. methanol started to evolve and the reaction mixture became semisolid. After two hours of heating the contents of the flask somewhat liquified. Towards the end of the reaction, nearly 25 ml of liquid consisting of methanol and xylene had been collected in the trap. The reaction mixture was cooled to room temperature and acidified with hydrochloric acid (500 ml of 6N). Stirring was continued for about 30 minutes until all the solid was dissolved. The xylene layer was separated and washed twice with water, then twice with aqueous sodium carbonate and then twice again with water. The xylene layer was removed by evaporation from the dibenzoylmethane (53.1 grams; 95% yield). Analysis by GLC showed the product to be 95% pure. This product after recrystallized from methanol had a melting point of 77°–78° C. The distillate (347.0 grams) containing xylene, methylbenzoate and water was subjected to azeotropic distillation.

Methyl benzoate (46.0 grames; 0.34 mol); acetophenone (30.0 grams; 0.25 mol); sodium methoxide (17.3 grames; 0.3 mol) and xylene 28.,0 grams) were added to the resulting mixture (347.0 grams) from the azetropic distillation. The reaction procedure set forth hereinabove was repeated with this reaction mixture giving dibenzoylmethane (54.2 grams; 92% yield) 92% pure by GLC analysis.

EXAMPLE 2

Preparation Of DibenzoylMethane

The procedure of Example 1 was repeated except the molar ratio of methylbenzoate to acetophenone was reduced from 4:1 to 2:1 by using (50% of the amount) of methyl benzoate (68 grams; 0.5 mol) used in Example 1. The yield of dibenzoylmethane product was 47 grams; 84% yield having a purity by GLC analysis of 95%.

EXAMPLE 3

Preparation Of DibenzoylMethane

Example 1 was repeated except that the amount of methyl benzoate used in the reaction mixture was 102 grams; 0.75 mol. The yield of dibenzoylmethane recovered as product was 53.6 grams; 92% yield. Its purity as determined by GLC was 89%.

Example 4 and 5 demonstrate the use of lower amounts of xylene solvent.

EXAMPLE 4

Preparation Of DibenzoylMethane

Example 1 was repeated except that the amount of xylene solvent used in the reaction mixture was reduced to 200 ml. 49.3 grams of dibenzoylmethane product representing a yield of 88% was recovered. Analysis by GLC showed it to be 95% pure.

EXAMPLE 5

Preparation Of Dibenzoylmethane

Example 3 was repeated except that the amount of xylene solvent used in the reaction mixture was 200 ml. Dibenzoylmethane product was recovered in an amount of 47.6 grams representing a yield of 85%. Analysis by GLC showed it to have a purity of 87%.

Example 6 demonstrates the recycling of the xylene solvent and the excess ester reactant.

EXAMPLE 6

Preparation Of Dibenzoylmethane

Acetophenone (150.0 grams; 1.25 mol), methyl benzoate (680.0 grams; 5.0 mol), sodium methoxide (86.5 grams; 1.6 mol) and xylene (1350 grams) were placed into a four-necked round bottom five-liter reaction flask equipped with stirrer, nitrogen addition adapter, thermometer and and Oldershaw column connected with a distillation head and a trap. The mixture was heated with stirring for 6 hours at 135°-140° C. under a blanket of nitrogen.

At 110°-120° C. the methanol started to evolve and the reaction mixture became semi-solid. The mixture liquified somewhat after 2 hours of heating. 118 grams of liquid containing xylene and methanol were collected in the trap. Then the reaction mixture was cooled to room temperature and acidified with hydrochloric acid (6N; 2500 ml). Stirring continued for about 30 minutes when all the solid was in solution. The xylene layer was separated, washed twice with water, twice with an aqueous solution of sodium carbonate and again twice with water. Dibenzoylmethane (246.3 grams; 88% yield) was recovered by evaporation of the xylene solution under vacuum. The distillate (ca. 2,000 ml) containing the excess methyl benzoate, xylene and water was placed in a separatory funnel and the water drawn off. The organic layer was subjected to azeotropic distillation for two hours with a hazy liquid (50 ml) collected in the Dean-Stark trap and discarded leaving a mixture (1470 gram) of xylene and methyl benzoate.

The refractive index of the distillate was found to be 1.5015 indicating that it contained methyl benzoate (485 grams; 33 weight percent) and xylene (985 grams; 67 weight percent). In order to substantiate that this mixture could be recycled into a reaction mixture of acetophenone and methyl benzoate, a portion of this mixture (406 grams), acetophenone (30.0 grams; 0.25 mol) and sodium methoxide (17.3 grams; 0.,3 mol) were reacted according to the above described procedure. Dibenzoylmethane (48.9 grams; 87% oxide) having a 91% purity by GLC analysis, was obtained using the same recovery procedure. The distillate (329.4 grams) had a refractive index of 1.5000 indicating a content of 25 weight percent methyl benzoate. Then a third reaction was performed by recycling said mixture (327.4 grams) containing methyl benzoat (82.0 gram) and xylene (247.4 grams) and adding additional methyl benzoate (54.0 grams), xylene (23.0 grams), acetophenone (30.0 grams; 0.25 mol) and sodium methoxide (17.3 grams). Dibenzoylmethane (44.0 grams) 86% of the theoretical yield having a purity of 94% by GLC analysis was obtained.

This recycling of xylene and excess dibenzoylmethane was continued for three additional cycles with the following results:

|  | Dibenzoylmethane Yield (Weight Percent) | Purity (By GLC) |
| --- | --- | --- |
| C-Cycle | 86 | 93 |
| D-Cycle | 80 | 92 |
| E-Cycle | 80 | 90 |

This experiment establishes that the recycling of xylene solvent and excess methylbenzoate can be performed without effecting the yield or purity of the aromatic beta-diketone product.

Example 7 demonstrates the use of sulfuric acid as a replacement for hydrochloric acid in the recovery procedure.

EXAMPLE 7

Preparation Of Dibenzoylmethane

Acetophenone (30 grams; 0.25 mol), methylbenzoate (130 grams, 1.0 mol), sodium methoxide (17.3 grams; 0.32 mol) and xylene (350 ml) were placed into a four necked round bottom one liter flask, equipped with stirrer, nitrogen addition adapter, thermometer and Oldershaw column connected with a distillation head and a trap. The solution was heated under a blanket of nitrogen to a temperature of about 130° C. At about 130° C., the mixture of xylene and methanol begins to come off the reaction mixture. Upon cooling the reaction mixture is acidified by adding sulfuric acid (21 ml) in water (100 ml). Once the material goes into solution it is transferred to a separatory funnel and the aqueous layer is removed. The xylene layer is washed with water (100 ml of a 10% solution). Then it is stirred at 120° C. and 15 mm Hg. The yield of dibenzoyl methane was 94 weight percent having a purity of 97%.

EXAMPLE 8

Preparation Of Benzoyl m-Methylbenzoylmethane

Acetophenone (30 grams; 0.25 mol) methyl m-methyltoluate (136 grams; 1.0 mol), xylene (300 ml) and sodium methoxide (17.3 grams; 0.3 mol) were placed into a four-necked round bottom one liter flask equipped as in Example 1. The mixture was heated with stirring to 135°-140° C. and maintained there for 6 hours under a blanket of nitrogen. The procedure set forth in Example 1 was used to recover the desired product, benzoyl m-methylbenzoylmethane (48 grams; 90% weight percent yield).

EXAMPLE 9

Preparation of Benzoyl p-Methylbenzoylmethane

Acetophenone (30 grams; 0,25 mol), methyl p-methyltoluate (136 grams; 1.0 mol), xylene (300 ml) and sodium methoxide (17.3 grams; 0.3 mol) were placed into a four-necked round bottom one liter flask equipped as in Example 1. The mixture was heated with stirring to 135°-140° C. and maintained there for 6 hours under a blanket of nitrogen. The procedure set forth in Example 1 was used to recover the desired product, benzoyl p-methylbenzoylmethane (40 grams; 67 weight percent yield) having a purity of 66%.

EXAMPLE 10

Preparation of Benzoylstearoylmethane

Acetophenone (30 grams; 0.25 mol), methylstearate (298 grams; 1.0 mol), xylene (300 ml) and sodium methoxide (17.3 grams; 0.3 mol) were placed into a four-necked, round bottom one liter flask equipped a in Example 1. The mixture was heated with stirring to 135°-140° C. and maintained there for 6 hours under a blanket of nitrogen. The procedure set forth in Example 1 was used to recover the desired product, benzoylstearoylmethane (43 grams; 45 weight percent yield) having a purity of 95%.

EXAMPLE 11

Preparation Of Benzoyl 3,5-Dimethylbenzoylmethane 3,5-dimethylacetophenone (37.1 grams; 0.75 mol), methylbenzoate (156 grams; 1.0 mol) and xylene (308.6 grams) were placed into a four-necked round bottom one liter flask equipped as in Example 1. Sodium methoxide (16.4 grams; 0.30 mol) was added to the stirred reaction mixture under a blanket of nitrogen and the mixture was heated to 135° C. As the temperature of the mixture reached 100° C., solution began coming over. The temperature was held at about 135° C. for 6 hours after which time it was cooled to room temperature. Sulfuric acid (375 ml of 10% solution) was added slowly over a 30 minute period with stirring. The xylene layer was separated and washed with water, then with sodium carbonate solution (100 ml of 10% solution) and again with water (100 ml). Xylene was stripped off at 175° C. resulting in the desired product, benzoyl 3,5-dimethylbenzoylmethane (51 grams; 63 weight percent yield) having a melting point of 48°-53° C..

EXAMPLE 12

Preparation Of Benzoyl 3,4-Methylenedioxybenzoylmethane 3,4-(methylenedioxy) acetophenone (41 grams; 0.25 mol); methylbenzoate (136 grams; 1.0 mol) and xylene (330.4 grams) were placed into a four-necked round bottom one liter flask equipped as in Example 1. Sodium methoxide (16.3 grams; 0.30 mol) was added slowly to the stirred reaction mixture which was then heated to 135° C. Solution (26 ml) came overhead and was recovered in the trap. The reaction mixture was stirred 5 hours at 135° C. Sulfuric acid (250 ml, 10%) was added in 30 minutes with stirring. Then the product mixture was washed three times with water, two times with sodium carbonate (100 ml, 10%) and again two times with water (100 ml). Then the solvent and excess methyl benzoate were stripped at 200° C. under full vacuum. The desired product, benzoyl 3,4-methylenedioxybenzoylmethane having a melting point of 65°-70° C. was recovered. Infrared and proton NMR spectra were consistent with the structure of the product.

As can be seen from the foregoing examples, a feature of the present process is the recirculation of excess ester reactant and solvent into a second reaction mixture of the acetophenone and ester reactants. This recirculation can be repeated as shown by examples. This enables maximum use of the reactants and solvent thus enhancing the efficiency of the process. Thus by separating the beta-diketone product from the reaction mixture by standard procedures known to the art for the separation of such materials, the solvent and excess ester reactant can be readily recycled into a second mixture of the reactants and solvent. Sufficient make-up solvent, reactants and sodium alkoxide need be added to this recycled stream for performing this reaction. This recycling of solvent and ester reactant can be repeated from the second reaction mixture into a third reaction mixture; from the third reaction mixture into a fourth reaction mixture, etc. for the preparation of high purity beta-ketone in high yield.

It will be understood that the embodiments of the present invention have been described as merely illustrative of a few of the applications of the principle of the present invention. Numerous modifications may be made by those skilled in the art without departing from the true spirit and scope of the invention.

What is claimed is:

1. A process for the preparation of an aromatic beta-diketone having the structural formula:

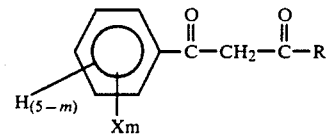

wherein X is selected from the group consisting of lower alkyl, lower alkoxy, lower alkylthio, chloro, bromo, nitro and methylenedioxy; and m is an integer from 0-3, provided that only one X is nitro or methylenedioxy; R is $(CH_2)pCH_3$ wherein p is an integer from about 11 to about 19; or

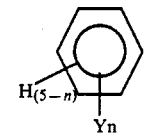

wherein Y is selected from the group consisting of lower alkyl, lower alkoxy, lower alkylthio, chloro, bromo and nitro and n is an integer from 0-3, provided that only one Y is nitro; which comprises mixing an acetophenone having the structural formula:

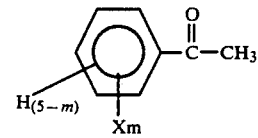

wherein X and m are as previously defined and a molar excess of an ester having the structural formula:

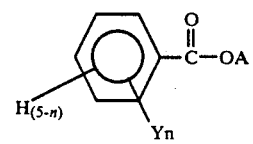

wherein Y and n are as previously described and A is lower alkyl or an alphatic ester having the structural formula:

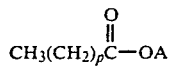

wherein A and p are as previously defined in the presence of a sodium alkoxide in an aromatic hydrocarbon solvent at a temperature between about 120° C. and about 170° C.

2. The process of claim 1 wherein the aromatic hydrocarbon solvent has a boiling point between about 120° C. and 170° C.

3. The process of claim 1 wherein the aromatic hydrocarbon solvent is xylene.

4. The process of claim 3 wherein R is:

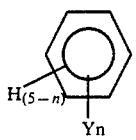

wherein Y is selected from the group consisting of lower alkyl, lower alkoxy, lower alkylthio, chloro, bromo and nitro and m is an integer from 0 to 3 provided that only one y is nitro.

5. The process of claim 4 wherein the sodium alkoxide has up to about 4 carbon atoms.

6. The process of claim 4 wherein n is o.

7. The process of claim 6 wherein m is o.

8. The process of claim 6 wherein X is methyl and m is 1 or 2.

9. The process of claim 4 wherein A is methyl or ethyl.

10. The process of claim 4 wherein the reaction temperature is about 140° C.

11. The process of claim 7 wherein the reaction temperature is about 140° C.

12. The process of claim 3 wherein the ester is the methyl or ethyl ester of stearic acid.

13. The process of claim 12 wherein the reaction temperature is about 140° C.

14. The process of claim 4 wherein the xylene solvent and unreacted ester of benzoic acid are separated from the aromatic beta-ketone product and recycled into a second reaction mixture of the same acetophenone and ester of benzoic acid.

15. The method of claim 14 wherein xylene solvent and unreacted ester of benzoic acid are separated from the aromatic beta-diketone product of the second reaction of an acetophenone and ester of benzoic acid and recycled into a third reaction mixture of the same acetophenone and ester of benzoic acid.

16. The method of claim 15 wherein the xylene solvent and unreacted ester of benzoic acid are separated from the aromatic beta-diketone product of the third reaction mixture of an acetophenone and ester of benzoic acid and recycled into a fourth reaction mixture of the same acetophenone and ester of benzoic acid.

17. The process of claim 3 wherein the xylene solvent and excess ester reactant are separated from the beta-diketone product and recycled into a second mixture of the acetophenone and ester reactants to prepare the aromatic beta-diketone and said recycling of the xylene and ester is repeated for a series of said reactions.

18. The process for the preparation of dibenzoylmethane which comprises reacting acetophenone and a lower ester of benzoic acid in xylene solvent at a temperature between about 120° C. and 170° C. in the presence of a sodium alkoxide condensing agent.

19. The process of claim 18 wherein the lower ester of benzoic acid is methyl or ethyl benzoate and the sodium alkoxide is sodium methoxide.

20. The process of claim 19 wherein the reaction is performed at atmospheric pressure.

* * * * *

REEXAMINATION CERTIFICATE (2443rd)
United States Patent [19]
Chisolm et al.

[11] B1 5,015,777

[45] Certificate Issued Dec. 20, 1994

[54] PROCESS FOR THE PREPARATION OF AROMATIC BETA-DIKETONES

[75] Inventors: Daniel R. Chisolm, Warwick, N.Y.; Richard A. Weiss, Parsippany; Leonid Rozov, Fairlawn, both of N.J.

[73] Assignee: Witco Corp., New York, N.Y.

Reexamination Request:
No. 90/003,159, Aug. 10, 1993

Reexamination Certificate for:
Patent No.: 5,015,777
Issued: May 14, 1991
Appl. No.: 430,563
Filed: Nov. 2, 1989

[51] Int. Cl.⁵ .............................................. C07C 45/45
[52] U.S. Cl. .................................. 568/314; 568/306; 568/42; 549/446

[58] Field of Search ............... 568/331, 314, 306, 42; 549/446

[56] References Cited
U.S. PATENT DOCUMENTS
4,562,067  12/1985  Hopp et al. .......................... 568/331

FOREIGN PATENT DOCUMENTS
52-126452  10/1977  Japan .................................. 568/333

*Primary Examiner*—James H. Reamer

[57] ABSTRACT

A process for the preparation of aromatic beta-diketones by the reaction of an acetophenone and a molar excess of an alphatic ester or an ester of benzoic acid in the presence of sodium alkoxide condensation agent in an aromatic hydrocarbon solvent. Also disclosed is a method of recycling the solvent and excess ester reactant after separation of the aromatic beta-diketone product.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 14 and 17 are cancelled.

Claims 1, 15, 16 and 18 are determined to be patentable as amended.

Claims 2 to 13, 19 and 20, dependent on an amended claim, are determined to be patentable.

New claims 21 to 31 are added and determined to be patentable.

1. A process for the preparation of an aromatic beta-diketone having the structural formula:

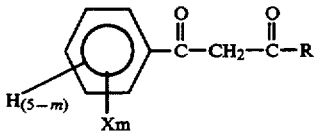

wherein X is selected from the group consisting of lower alkyl, lower alkoxy, lower alkylthio, chloro, bromo, nitro and methylenedioxy; and m is an integer from 0–3, provided that only one X is nitro or methylenedioxy; R is $(CH_2)_p CH_3$ wherein p is an integer from about 11 to about 19; or

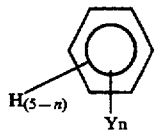

wherein Y is selected from the group consisting of lower alkyl, lower alkoxy, lower alkylthio, chloro, bromo and nitro and n is an integer from 0–3, provided that only one Y is nitro; which comprises mixing an acetophenone having the structural formula:

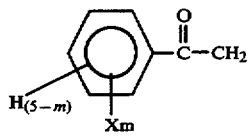

wherein X and m are as previously defined and *substantially greater than a 2:1 molar excess* of an ester having the structural formula:

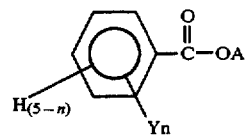

wherein Y and n are as previously described and A is *a* lower alkyl or an aliphatic ester having the structural formula:

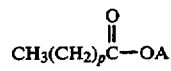

wherein A and p are as previously defined in the presence of a sodium alkoxide in an aromatic hydrocarbon solvent at a temperature between about 120° C. and about 170° C; *and wherein the solvent and unreacted ester are separated from the aromatic beta-ketone product and recycled into a second reaction mixture of the same acetophenone and ester.*

15. The method of claim [14] *1* wherein [xylene] *the* solvent and unreacted ester [of benzoic acid] are separated from the aromatic beta-diketone product of the second reaction of an acetophenone and ester [of benzoic acid] and recycled into a third reaction mixture of the same acetophenone and ester [of benzoic acid].

16. The method of claim 15 wherein the [xylene] solvent and unreacted ester [of benzoic acid] are separated from the aromatic beta-diketone product of the third reaction mixture of an acetophenone and ester [of benzoic acid] and recycled into a fourth reaction mixture of the same acetophenone and ester [of benzoic acid].

18. [The] *A* process for the preparation of dibenzoylmethane which comprises reacting acetophenone and a lower ester of benzoic acid in xylene solvent at a temperature between about 120° C. and 170° C. in the presence of a sodium alkoxide condensing agent *wherein the molar ratio of said ester to said acetophenone is substantially greater than 2:1.*

*21. The process of claim 1 wherein said aromatic hydrocarbon solvent is selected from the group consisting of ethyl benzene, cymene, diethylbenzene, dimethylethylbenzene, amyltoluene, toluene, trimethylbenzene and xylene, and mixtures thereof.*

*22. The process of claim 1 wherein the aromatic hydrocarbon solvent is cymene.*

*23. A process for the preparation of dibenzoylmethane which comprises reacting acetophenone and a lower ester of benzoic acid in an aromatic hydrocarbon solvent at a temperature between about 135° C. and 170° C. in the presence of a sodium alkoxide condensing agent wherein the molar ratio of said ester to said acetophenone is substantially greater than 2:1.*

*24. The process of claim 23 wherein said aromatic hydrocarbon solvent is cymene.*

*25. The process of claim 23 wherein said ratio is greater than 3:1.*

*26. The process of claim 23 wherein said ratio is about 4:1.*

*27. The process of claim 23 wherein the reaction temperature is between about 135° C. and about 140° C.*

*28. The process of claim 23 wherein the solvent and excess ester reactant are separated from the dibenzoylme-* thane product and recycled into another reaction mixture of acetophenone and said ester reactant for the preparation of dibenzoylmethane.

29. The process of claim 23 wherein said sodium alkoxide is present in a molar amount greater than the molar amount of said acetophenone and less than the molar amount of said ester reactant.

30. A process for the preparation of dibenzolymethane in yields of greater than 90% as measured before crystallization which comprises reacting acetophenone and methylbenzoate in cymene at a temperature between about 135° and 140° C. in the presence of sodium methoxide, wherein the molar ratio of said methylybenzoate to said acetophenone is about 4:1, and the reaction is preformed at atmospheric pressure.

31. The process of claim 30 wherein said sodium methoxide is present in a molar amount greater than the molar amount of said acetophenone and less than the molar amount of said methylbenzoate.

* * * * *